(12) United States Patent
Seo et al.

(10) Patent No.: US 8,288,130 B2
(45) Date of Patent: *Oct. 16, 2012

(54) POLYPEPTIDE CLEAVAGE PROCESS

(75) Inventors: Jin Seog Seo, Brampton (CA); Daniel Strydom, Eagle, NE (US); Barton Holmquist, Eagle, NE (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/795,073

(22) Filed: Jun. 7, 2010

(65) Prior Publication Data

US 2010/0311947 A1 Dec. 9, 2010

Related U.S. Application Data

(60) Division of application No. 10/997,762, filed on Nov. 24, 2004, now Pat. No. 7,771,966, which is a continuation of application No. PCT/US03/16468, filed on May 23, 2003.

(60) Provisional application No. 60/383,488, filed on May 24, 2002.

(51) Int. Cl.
 *C12P 13/24* (2006.01)
(52) U.S. Cl. .......... 435/107; 435/7.1; 530/344; 530/345
(58) Field of Classification Search ........................ None
 See application file for complete search history.

(56) References Cited

U.S. PATENT DOCUMENTS

| 5,352,771 | A | 10/1994 | Kostic |
| 6,660,758 | B1 | 12/2003 | Nicolaou |
| 6,660,763 | B2 | 12/2003 | Tang |
| 7,592,432 | B2 * | 9/2009 | Holmquist et al. ........... 530/402 |

OTHER PUBLICATIONS

Zhu, L. et al., "Site-Specific Hydrolytic cleavage of cytochrome c and of its heme undecapeptide, promoted by coordination complexes of palladium (II)", Journal of the American Chemical Society, 116(12) (1994), 5218-5224.
"U.S. Appl. No. 10/997,081, Response to Final Office Action filed Feb. 15, 2008", 10 pgs.
"U.S. Appl. No. 10/997,822, Non-Final Office Action mailed Apr. 30, 2008", 10 pgs.
Parac, T.N. et al., "New Regioselectivty in the Cleavage of Histidine-Containing Peptides by Palladium (II), Complexes Studied by Kinetic Experiments and Molecular Dynamics Simulations", J. Am. Chem. Soc. 121 (1999), 3127-3135.
International Written Opinion dated Oct. 7, 2004 in Serial No. PCT/US03/16468, 3 pgs.
International Search Report dated Jan. 15, 2004 in Serial No. PCT/US03/16468, 3 pgs.
International Preliminary Examination Report dated Jan. 28, 2005 in Serial No. PCT/US03/16468, 4 pgs.
Rau, T. et al., "Complex Formation and Ligand Substitution Reactions of (2-Picolylamine)palladium(II) with various biologically relevant ligands. Characterization of (2-picolylamine)(1,1-cyclobutanedicarboxylato)palladium(II)", Inorganic Chemistry 36 (1997), 1454-1463.
Hohmann, H. et al., "Rate and equilibrium data for substitution reactions of diaqua(ethylenediamine)palladium(II) with chloride in aqueous solution", Inon Chim. Acta. 174(1). (1990). 87-92.
F. Dou et al., "Preliminary study on the cleavage of chimeric protein GST-CMIV with paddadate(II) complex", Prep. Biochem. and Biotechnol. 301(1) (2000) 69-78.
PCT Search Report in Application No. PCT/US03/16468 (Dec. 12, 2003).
Drexler, C. et al., Palladium(II) and platinum (II) complexes with 1,5-dithiacycloctane(dtco)—structures of Pd(dtco)C12 and Pd(dtco2)(NO3)2 and kinetics of ligand substitution in [Pd(dtco2)]2plus by bidenate ligands, Inorganic Chemistry, 30c, (1991), 1297-1302.
Search Report, European Patent Application No. 03736710/0, dated Oct. 1, 2007, 6 pages.
U.S. Appl. No. 10/997,822, Response to Restriction Requirement filed Jul. 25, 2007, 10 pgs.
Written Opinion, International Application No. PCT/US03/16468, dated Jan. 28, 2005, 4 pgs.
Search Report, International Application No. PCT/US03/16468, dated Jan. 15, 2004, 1 pg.
Milovic, N.M. et al., "Palladium(II) complexes, as synthetic peptidases, Regioselectively cleave the second peptide bond "Upstream" from methionine and histidine side chains", Journal of the American Chemical Society, 124(17), May 1, 2002 4759-4769.
Djuran M.I et al., Hydrolysis of amide bond in histidine-containing peptides promoted by chelated amino acid palladium(II) complexes; dependence of hydrolytic pathway on the coordination modes of the peptides, Polyhedron, 18(27), Sep. 14, 1999, 3611-3616.
Milovic, N. M. et al., "Palladium(II) and platinum(II) complexes as synthetic peptidases", Met Ions Biol. Syst. 38 (2001) 145-186.
International Application No. PCT/US03/16647, International Preliminary Examination Report mailed Sep. 7, 2004, 8 pgs.
U.S. Appl. No. 10/997,081, Non Final Office Action mailed May 2, 2007, 8 pgs.
U.S. Appl. No. 10/997,822, Response to Office Action mailed Oct. 4, 2007, 12 pgs.
International Application No. PCT/US03/16648, International Preliminary Examination Report mailed Dec. 13, 2004, 4 pgs.
International Application No. PCT/US03/16648, International Written Opinion mailed Sep. 7, 2004, 6 pgs.
International Application No. PCT/US03/16648, International Search Report mailed May 27, 2004, 6 pgs.
U.S. Appl. No. 10/997,081, Final Office Action mailed Jan. 4, 2008, FOAR, 10 pgs.
U.S. Appl. No. 10/997,081, Response to Non Final Office Action filed Sep. 4, 2007, 10 pgs.
International Application No. PCT/US03/16647, International Search Report mailed Jul. 2, 2004, 4 pgs.
Non Final Office Action mailed Oct. 4, 2007, U.S. Appl. No. 10/997,822, OARN, 12 pgs.

* cited by examiner

*Primary Examiner* — Hope Robinson
(74) *Attorney, Agent, or Firm* — Mueting Raasch & Gebhardt PA

(57) ABSTRACT

A palladate palladium-promoted hydrolytic polypeptide cleavage process which selectively cleaves the polypeptide at a Cys-His cleavage site comprising solubilizing the polypeptide in a reaction mixture comprised of a palladate palladium promoter dissolved in a high-concentration acidic organic acid solvent.

20 Claims, 10 Drawing Sheets

```
  1 ATGGCTAGCA TGACTGGTGG ACAGCAAATG GGTCGCGGGAT CCGGCCAGGG   Frame 1
    M  A  S   M  T  G  G   Q  Q  M    G  R  G  S     G  Q  G 51 ACAGGCTCAA TATCTAGCGG CCTCCTTGGT TGTGTTCACC AACTACTCGG   Frame 1
    Q  A  Q    Y  L  A  A  S  L  V    V  F  T     N  Y  S  G 101 GCGACACGGC CAGCCAGGTG GACGTTAACG GTCCGCGTGC TATGGTCGAC   Frame 1
    D  T  A    S  Q  V     D  V  N  G  P  R  A    M  V  D 151 GACGACGACA AATGCCACTA CGCTGACGCT ATCTTCACCA ACTCTTACCG   Frame 1
    D  D  D  K  C  H  Y    A  D  A    I  F  T  N  S  Y  R 201 TAAAGTTCTG GGTCAGCTGT CTGCTCGTAA ACTGCTGCAG GACATCATGT   Frame 1
    K  V  L    G  Q  L  S  A  R  K    L  L  Q    D  I  M  S 251 CCCGTCAGCA GGGTGAATCT AACCAGGAAC GTGGTGCTCG TGCTCGTCTG   Frame 1
    R  Q  Q    G  E  S    N  Q  E  R  G  A  R     A  R  L 301 GCATAA
    A  *     Frame 1
```

Fig. 6

```
  1 ATGGCTAGCA TGACTGGTGG ACAGCAAATG GGTCGCGGAT CCGGCCAGGG   Frame 1
    M  A  S   M  T  G  G   Q  Q  M    G  R  G  S    G  Q  G 51 ACAGGCTCAA TATCTAGCGG CCTCCTTGGT TGTGTTCACC AACTACTCGG   Frame 1
    Q  A  Q    Y  L  A  A   S  L  V    V  F  T    N  Y  S  G 101 GCGACACGGC CAGCCCAGGTG GACGTTAACG GTCCGCGTGC TATGGTCGAC   Frame 1
    D  T  A    S  Q  V    D  V  N  G   P  R  A    M  V  D 151 GACGACGACA AATGCCACTA CGCTGACGCT ATCTTCACCA ACTCTTACCG   Frame 1
    D  D  D  K   C  H  Y   A  D  A    I  F  T  N   S  Y  R 201 TAAAGTTCTG GGTCAGCTGT CTGCTCGTAA ACTGCTGCAG GACATCATGT   Frame 1
    K  V  L    G  Q  L  S   A  R  K    L  L  Q    D  I  M  S 251 CCCGTCAGCA GGGTGAATCT AACCAGGAAC GTGGTGCTCG TGCTCGTCTG   Frame 1
    R  Q  Q    G  E  S    N  Q  E  R   G  A  R    A  R  L 301 TGCCACTAA
    C  H  *   Frame 1
```

*Fig. 7*

```
  1 ATGGCTAGCA TGACTGGTGG ACAGCAAATG GGTCGCGGAT CCGGCCAGGG    Frame 1
    M  A  S   M  T  G  G   Q  Q  M    G  R  G  S    G  Q  G 51 TCAGGCTCAA TATCTGGCTG CCTCCCTGGT TGTGTTCACC AACTACTCGG    Frame 1
     Q  A  Q   Y  L  A  A   S  L  V    V  F  T    N  Y  S  G 101 GCGACACGGC CAGCCAGGTG GACGTTAACC CGGAATTCTC TGTTGGTGGT    Frame 1
     D  T  A   S  Q  V    D  V  N  P   E  F  S    V  G  G 151 GGTGGTGGTC CGCGTTGCCA CTCTGTTTCT GAAATCCAGC TGATGCACAA    Frame 1
    G  G  G  P   R  C  H   S  V  S    E  I  Q  L   M  H  N 201 CCTGGGTAAA CACCTGAACT CTATGGAACG TGTTGAATGG CTGCGTAAAA    Frame 1
    L  G  K    H  L  N  S   M  E  R   V  E  W    L  R  K  K 251 AACTGCAGGA CGTTCACAAC TTCTAA    Frame 1
    L  Q  D    V  H  N    F  *
```

Fig. 8

```
  1 ATGGCTAGCA TGACTGGTGG ACAGCAAATG GGTCGCGGGAT CCGGCCAGGG    Frame 1
    M  A  S    M  T  G  G    Q  Q  M     G  R  G  S     G  Q  G 51 TCAGGCTCAA TATCTGGCTG CCTCCCTGGT TGTGTTCACC AACTACTCGG    Frame 1
    Q  A  Q     Y  L  A  A    S  L  V     V  F  T     N  Y  S  G 101 GCGACACGGC CAGCCAGGTG GACGTTAACC CGGAATTCTC TGTTGGTGGT    Frame 1
    D  T  A     S  Q  V     D  V  N  P     E  F  S     V  G  G 151 GGTGGTGGTC CGCGTTGCCA CTCTGTTTCT GAAATCCAGC TGATGCACAA    Frame 1
    G  G  G  P    R  C  H     S  V  S     E  I  Q  L    M  H  N 201 CCTGGGTAAA CACCTGAACT CTATGGAACG TGTTGAATGG CTGCGTAAAA    Frame 1
    L  G  K     H  L  N  S    M  E  R     V  E  W     L  R  K  K 251 AACTGCAGGA CGTTCACAAC TTCGTTGCTC TGGGTGCTCC GCTGGCTCCG    Frame 1
    L  Q  D     V  H  N     F  V  A  L    G  A  P     L  A  P 301 CGTGACGCTG GTTCCCAGCG TCCGCGCGTAAA AAAGAAGACA ACGTTCTGGT    Frame 1
    R  D  A  G    S  Q  R     P  R  K     K  E  D  N    V  L  V 351 TGAATCCCAC GAAAAATCCC TGGGTGAAGC TGACAAAGCT GACGTTAACG    Frame 1
    E  S  H     E  K  S  L    G  E  A     D  K  A     D  V  N  V 401 TTCTGACCAA AGCTAAATCC CAGTAA                                Frame 1
    L  T  K     A  K  S     Q  *
```

*Fig. 9*

POLYPEPTIDE CLEAVAGE PROCESS

This is a divisional application of U.S. patent application Ser. No. 10/997,762 filed Nov. 24, 2004, which is a continuation of PCT/US03/16468 filed May 23, 2003 which claims priority to U.S. 60/383,488 filed May 24, 2002, now U.S. Pat. No. 7,771,966.

FIELD OF THE INVENTION

The invention provides highly specific, conformationally independent, palladium promoted hydrolytic cleavage of polypeptides, including cleavage of relatively insoluble chimeric proteins in the form of inclusion bodies.

BACKGROUND OF THE INVENTION

It is well known that the production of peptides of less than about 100 amino acids in length by expression of peptide-encoding DNA in a recombinant host cell such as *E. coli* is plagued by enzymatic degradation of the expressed peptide within the host cell, which often results in partial or complete loss of the peptide. The most commonly employed means to overcome this problem is to insolubilize the peptide within the host cell. This can be affected by expressing the peptide as a chimeric protein in which the peptide is linked to a fusion partner. Normally, the fusion partner will be fused to the N-terminus of the peptide. The chimeric protein forms inclusion bodies within the cell, within which the peptide is protected from degradation by proteolytic enzymes. Once the inclusion bodies are recovered from the host cell, the peptide must be separated from the leader sequence, purified and recovered in an active form. Cleavage from the leader sequence may be accomplished by placing a sequence of amino acids at the junction of the leader and the peptide which are specifically recognized and cleaved under appropriate conditions, e.g. acid cleavage or enzymatic cleavage.

For example, introduction of acid-labile aspartyl-proline linkage between the two segments of a chimeric protein facilitates cleavage at low pH. This technique does not work if the product peptide, which is to be cleaved from the polypeptide, is not acid-labile. Chimeric proteins comprising hormones such as insulin and somatostatin have been cleaved with cyanogen bromide, which is specific for the carboxyl side of methionine residues. This method is not suitable when the product peptide contains methionine residues.

Cleavage of chimeric proteins by site-specific proteolysis has also been investigated. Chimeric proteins containing a chicken pro alpha.-2 collagen linker could be specifically degraded by purified microbial collagenase to release the components of the chimeric protein. Use of proteolytic enzymes is expensive, product peptide cleavage yield is frequently low, and it can prove difficult to separate the enzyme from a desired peptide product. Other methods for purification and recovery of a desired recombinant protein include construction of a poly-arginine tail at the C-terminus of the polypeptide. The arginine residues increase the overall basicity of the protein, which facilitates purification by ion exchange chromatography. Subsequent removal of the poly-arginine tail by carboxypeptidase B regenerates the desired protein and allows purification from basic contaminants due to the reduction in pI of the desired protein.

Acid cleavage can be accomplished by placing a specific dipeptide at the junction of the leader sequence and the peptide. Selection of the second amino acid will determine the rate at which the dipeptide bond is cleaved under acidic conditions. Of course, if the desired peptide contains any internal dipeptide sequences that are acid cleavable, then the cleavage site at the junction of the leader and the peptide must undergo acid cleavage at a substantially greater rate than the internal cleavage in order to avoid unacceptable loss of yield.

Zhu et al., *J. Am. Chem. Soc.* 116: 5218 (1994), describe selective cleavage of cytochrome-c at S-hemo-Cysteinyl-Histidine (Cys(hemo)-His) using certain palladate(II)(Pd II) complexes under acidic conditions. Under the reaction conditions described in Zhu et al., cleavage of cytochrome c took 2 days at 40° C. and resulted in a cleavage yield of only 35-50%. (SDS-PAGE analysis in fact indicated some degree of non-specific cleavage; as the molar ratio of Pd to protein was increased from 1:1 to 4:1, there was an indication of cleavage at a site other than the Cys(hemo)-His sequence.)

Zhu et al. state at p. 5220 that 100 mM $HBF_4$, $HClO_4$, and $CF_3COOH$, or 70% formic acid, cleaved cytochrome-c. The reference thereafter concludes that cleavage was inhibited by the presence of chloride ions, a notable drawback as proteins purified from biological systems will almost invariably contain chloride ions. Notably, Zhu et al. at p. 5219 conclude that the rate of hydrolysis depended on conformational aspects of cytochrome c (i.e., cleavage was thought to be affected by the size of the cleaved peptide fragment and hence, the sequence of the polypeptide to be cleaved).

Dou, et al., "Preliminary Study On The Cleavage Of Chimeric protein GST-CMN With Palladate(II) complex", *Prep. Biochem & Biotechnol.*, 301(1): 69-78 (2000) ("Dou, et al."), describe palladate promoted hydrolytic cleavage of a cecropin CMIV chimeric protein using formic acid, acetic acid, phosphoric acid and $HBF_4$ and $[Pd(en)(H_2O)_2]^{2+}$ Dou, et al. sought to cleave their chimeric protein specifically at two cleavage sites: Cys-His-Lys and Cys-His-Arg. According to Dou, et al., p. 76, only the $HBF_4$ reaction media cleaved the chimeric protein at the experimental conditions of 40° C. and reaction time of 48 hours. The cleavage in $HBF_4$ was said to be pH-dependent or independent depending on the amino acid adjacent to Cys-His: cleavage at Cys-His-Lys was pH-independent while cleavage at Cys-His-Arg was pH-dependent. Id. Further, cleavage at either site in $HBF_4$ was temperature dependent; when the temperature was increased to 60° C. the chimeric protein solubilized and it was no longer possible to cleave selectively. Id. Dou, et al. understood that their reaction would be strongly inhibited by the presence of chloride ions and employed an extra ion-exchange chromatography purification step before the cleavage reaction.

Read in context, Dou et al. and Zhu et al. would suggest that palladate promoted hydrolytic cleavage of polypeptides is not assured in concentrated acidic organic media, but instead is dependent upon the sequence of the polypeptide to be cleaved, reaction temperature and the possible inhibitory effects of chloride-containing species, including highly useful chloride-containing palladates. Dou et al. imply that solubilization of their chimeric protein results in a loss of cleavage specificity.

In sum, known hydrolytic polypeptide cleavage processes would suggest that even in concentrated acidic media, either the sequence of the polypeptide, the reaction media temperature or ionic species present in the reaction media could limit cleavage yield and specificity.

OBJECTS OF THE INVENTION

It is an object of the instant invention to provide an improved process for the hydrolytic cleavage of polypeptides.

It is an additional object of the instant invention to provide an improved process for the hydrolytic cleavage of polypeptides which is highly specific and which is not affected by the polypeptide sequence or the size of the cleaved peptide product.

It is an additional object of the instant invention to provide an improved process for the hydrolytic cleavage of polypeptides that have been expressed recombinantly in the form of chimeric proteins, especially chimeric proteins in the form of relatively insoluble inclusion bodies.

It is a still further object of the instant invention to provide an improved process for the hydrolytic cleavage of polypeptides which is highly specific, which does not generate unwanted side-products and which uses chloride-containing palladate species.

SUMMARY OF THE INVENTION

In accordance with the above-stated objects, the process of the instant invention provides a highly site-specific process for palladium-promoted hydrolytic cleavage of polypeptides under reaction conditions that are relatively insensitive to variations in reactant concentration, temperature or pH. The process is conformationally and sequence-independent, i.e., it achieves high cleavage yield irrespective of the type of amino acid groups adjacent to the specified cleavage site. Further, the process of the instant invention cleaves polypeptides under conditions which limit the formation of unwanted side-products and which enable the use of chloride-containing catalysts and reaction-media. The process may be employed to cleave, with a high degree of specificity, a single-copy recombinant polypeptide, a multi-copy recombinant polypeptide or a single or multi-copy recombinant chimeric protein construct. Consequently, the process can produce numerous cleaved peptide fragments suitable for further processing.

More specifically, the invention provides a process for cleaving a polypeptide at a Cys-His cleavage site in a reaction medium comprising a concentrated organic acid and a palladium promotor. In one embodiment, a chimeric protein comprised of a leader sequence joined by a Cys-His cleavage site to the N-terminus of the peptide is cleaved by solubilizing the chimeric protein in a reaction mixture comprised of a palladium promotor dissolved in a high-concentration organic acid solvent selected from the group consisting of monocarboxylic acids such as acetic acid, propionic acid, butyric acid and pyruvic acid; hydroxysubstituted acids such as lactic acid, tartaric acid and citric acid; dicarboxylic acids such as oxalic acid, malic acid, maleic acid, malonic acid, fumaric acid, glutaric acid, adipic acid, succinic acid and pimelic acid; tricarboxylic acids such as tricarballylic acid; sugar acids such as glucuronic acid and other uronic acids; aldonic acids such as gluconic acid; and aldaric acids such as saccharic acid. The concentration of the organic solvent in the reaction mixture is between about 1 to about 22 molar. Acetic acid, citric acid, lactic acid, maleic acid, malonic acid, propionic acid, pyruvic acid, tartaric acid, and tricarballylic acid are preferred acids. These reaction media solubilize chimeric proteins or inclusion bodies previously considered to be relatively insoluble and such solubilization, rather than decreasing the specificity of cleavage, actually leads to improved yields of cleaved peptide. Importantly, the process cleaves such chimeric proteins in a manner that facilitates additional processing necessary to post-translationally modify the cleaved peptide, e.g., amidation.

In preferred embodiments (i) the molar ratio of palladium promotor to inclusion body in the reaction media is from about 2:1 to about 20:1, (ii) the reaction mixture temperature is maintained at about 50° C. to about 70° C.; and (iii) the solvent is an organic acid present in the reaction medium in a concentration of from 1 to 22 M.

Palladium promoted acid cleavage in accordance with the process of the instant invention is facilitated by the use of these high concentration acidic organic solvents which solubilize inclusion bodies such as T7tag-Vg-$D_4$K-CH-GRF(1-44)-CH (SEQ ID NO:1), T7tag-Vg-$D_4$K-CH-GRF(1-44)-A (SEQ ID NO:2), T7tag-Vg-$G_5$PR-CH-PTH(1-34) (SEQ ID NO:3) or T7tag-Vg-$G_5$PR-CH-PTH (1-84) (SEQ ID NO:4).

BRIEF DESCRIPTION OF THE DRAWINGS

FIG. 6 illustrates the nucleotide (SEQ ID NO:13) and amino acid (SEQ ID NO:14) sequence of the chimeric protein T7tag-Vg-$D_4$K-CH-GRF(1-44)-Ala (SEQ ID NO:2). The stop codon is indicated by a star.

FIG. 7 illustrates the nucleotide (SEQ ID NO:15) and amino acid (SEQ ID NO:16) sequence of the chimeric protein T7tag-Vg-$D_4$K-CH-GRF(1-44)-CH (SEQ ID NO:1). The stop codon is indicated by a star.

FIG. 8 illustrates the nucleotide (SEQ ID NO:17) and amino acid (SEQ ID NO:18) sequence of the chimeric protein T7tag-Vg-$G_5$PR-CH-PTH(1-34) (SEQ ID NO:3). The stop codon is indicated by a star.

FIG. 9 illustrates the nucleotide (SEQ ID NO:19) and amino acid (SEQ ID NO:20) sequence of the chimeric protein T7tag-Vg-G5PR-CH-PTH(1-84) (SEQ ID NO:4). The stop codon is indicated by a star.

DETAILED DESCRIPTION OF THE INVENTION

Figure 1:
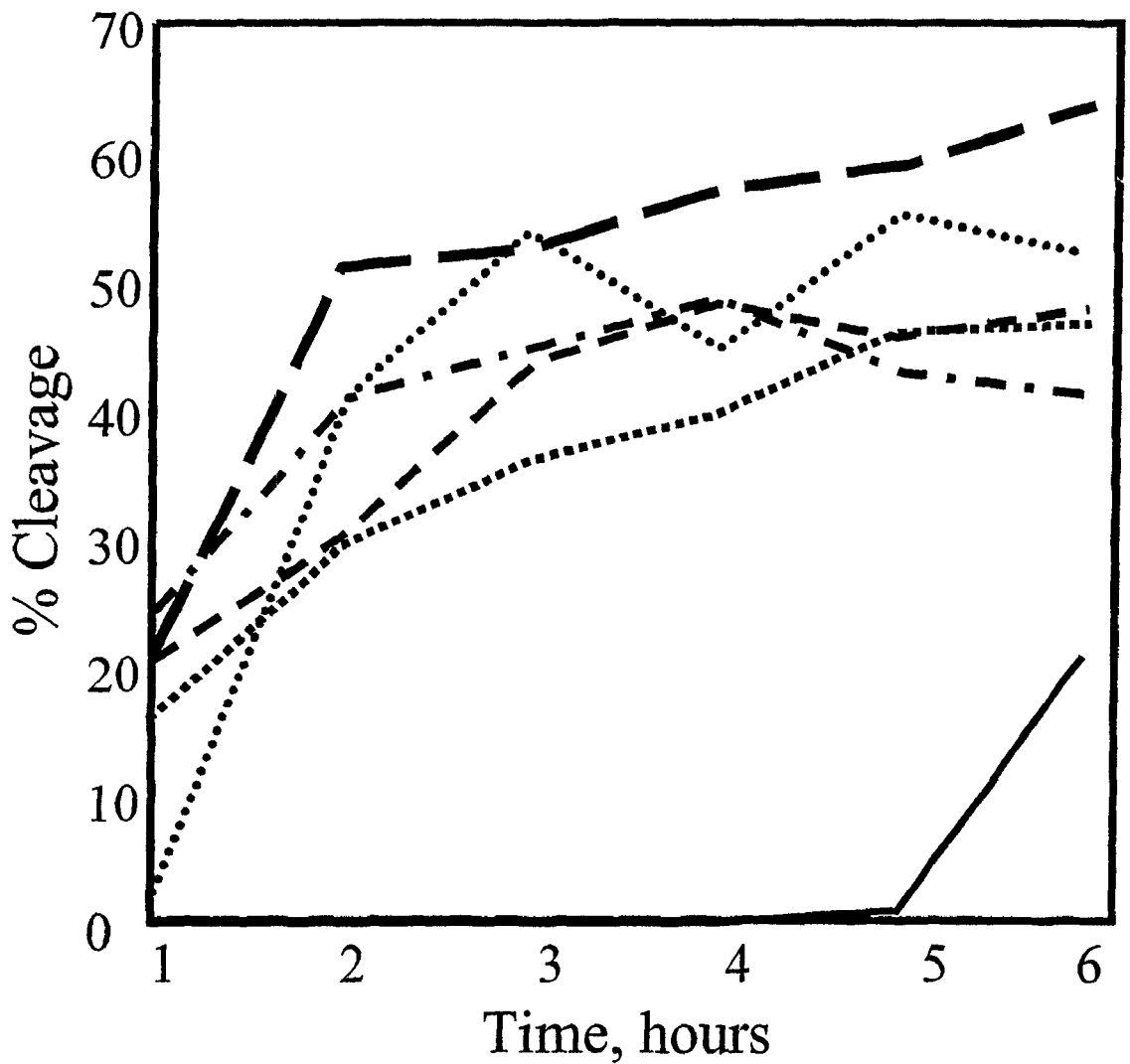
FIG. 1 illustrates tetrachloropalladate cleavage of T7tag-$D_4$K-CH-GRF(1-44)-CH (SEQ ID NO:5) over the course of 6 hours in various organic acids. The various acids are as follows: Malonic (long dashes), Tartaric (circular dots), Pyruvic (alternating dashes), Citric (short dashes), Malic (square dashes), and Maleic (solid line).

It will be appreciated that the process of the instant invention may be employed to cleave naturally occurring peptides, synthetically derived peptides, and recombinantly derived peptides. The embodiments described in detail hereinafter relate to cleavage of recombinantly expressed chimeric proteins in the form of inclusion bodies.

The process of the instant invention can be applied to cleave chimeric proteins which have been recombinantly expressed in a microbial host cell using known techniques of recombinant DNA production and which have been recovered from the host cell in the form of an inclusion body. Any suitable host cell known to be useful for the expression of proteins by recombinant DNA methods may be employed to express such chimeric proteins, including prokaryotic and eukaryotic host cells and cell lines. *E. coli* is a preferred host cell. The host cell contains an expression vector which encodes the chimeric protein under the control of a regulatory sequence which is capable of directing its expression in the host, as well as an origin of replication that is functional in the host cell. The vector may contain other DNA sequences conventionally employed in recombinant DNA technology such as sequences encoding selectable markers. Methods for expressing a foreign gene in a host organism also are well known in the art (see, e.g., Maniatis et al. *Molecular Cloning: A Laboratory Manual*, Cold Spring Harbor Laboratory Press, $2^{nd}$ ed., 1989).

The gene encoding a particular polypeptide can be constructed by chemically synthesizing the entire nucleotide sequence, by amplification, such as by the polymerase chain reaction (PCR), or by cloning the gene of interest. The gene is then subcloned into an appropriate expression vector. Cloning vectors, expression vectors, plasmids, and viral vectors are well known in the art (see, e.g., Maniatis et al., supra, and Goedell, *Methods in Enzymology*, Vol. 185 (Academic Press 1990)). Example 1 provides a description of the preparation of a $T_7$-based expression system useful for high-level expression of mammalian proteins in *E. coli*.

The host cell containing the expression vector is grown and the chimeric protein expressed under appropriate conditions. The conditions for growth of the host cell and expression of the chimeric protein will vary depending on various factors such as the host cell employed, the promoter and the particular chimeric protein being expressed. Those skilled in the art are capable of determining the appropriate conditions for the particular host/vector system employed. Methods for expressing a foreign gene in a host organism also are well known in the art (see, e.g., Maniatis et al. *Molecular Cloning: A Laboratory Manual*, Cold Spring Harbor Laboratory Press, $2^{nd}$ ed., 1989). The gene encoding a particular polypeptide can be constructed by chemically synthesizing the entire nucleotide sequence, by amplification, such as by the polymerase chain reaction (PCR), or by cloning the gene of interest. The gene is then subcloned into an appropriate expression vector. Cloning vectors, expression vectors, plasmids, and viral vectors are well known in the art (see, e.g., Maniatis et al., supra, and Goedell, *Methods in Enzymology*, Vol. 185 (Academic Press 1990)). Example 1 provides a detailed description of the preparation of a T7-based expression system useful for high-level expression of mammalian proteins in *E. coli*.

When a polypeptide is prepared by recombinant techniques, one can add a Cys-His cleavage site within the sequence of the polypeptide by incorporating or mutating the appropriate nucleotides into the encoding nucleic acid by any of various methods including, for example, site-directed mutagenesis. Such a Cys-His sequence can provide a site for cleavage by palladium complexes as described herein. Recombinant methods can also be used to generate a nucleic acid encoding a protein with a repeating polypeptide sequence, each sequence separated by a Cys-His cleavage site. In this case, palladium complex-promoted cleavage can occur at multiple Cys-His sites in the polypeptide, releasing multiple copies of the desired peptide.

Application of the process of the instant invention to peptides or proteins that contain a Cys-His sequence results in selective cleavage at the Cys-His sequence. Alternatively, to facilitate cleavage, a Cys or a His residue may be incorporated into a site adjacent to the residue present in a peptide to create a Cys-His cleavage site, e.g., by site-specific mutagenesis. Thus, selective cleavage can then be achieved at the incorporated Cys-His site to produce peptide fragments. In the rare case in which a desired peptide or protein contains an intrinsic Cys-His sequence where palladium-promoted cleavage would cleave the peptide or protein into undesired fragments, site-specific mutagenesis could be used to alter either the Cys or the His residue to another amino acid to prevent cleavage at such site.

Thus, the process of the instant invention provides for the cleavage of chimeric proteins comprising peptides which include, but are not limited to, the glucagon-like peptide-1 (GLP-1), glucagon-like peptide-2 (GLP-2), parathyroid hormone (PTH), parathyroid hormone related protein, growth hormone releasing hormone (GRF), adrenocorticotropic hormone (ACTH), enkephalins, endorphins, exendens, amylins, various opioid peptides, frog skin antibiotic peptides, such as gaegurins 5 and 6, brevinin 1, the ranatuerins 1 through 9, and the esculetins, glucose-dependent insulinotropic polypeptide (GIP), glucagon, motilin, thymopoietins, thymosins, ubiquitin, serum thymic factor, thymic humoral factor, neurotensin, tuftsin, and fragments and derivatives of these peptides.

Many polypeptides have an amide at their C-terminal and/or an -S-S-linkage in the molecule. The precursor non-amidated or reduced forms of these peptides, respectively, can be expressed as a fusion construct with a Cys-His cleavage site incorporated and subjected to cleavage by palladium complexes in accordance with the process of the instant invention. The product can then be amidated or oxidized to produce the final desired molecule. Examples of such peptides include gastrin, calcitonin, luteinizing-hormone-releasing hormone, pancreatic polypeptide, endothelin, corticotropin releasing factor, neuropeptide Y, atrial naturetic peptide, amylin, galanin, somatostatins, vasoactive intestinal peptide, insulin, and fragments and derivatives of these peptides.

Examples of leader sequences which can be employed with chimeric proteins include a signal sequence such as that used to direct secretion of a protein from a cell, the N-terminal portion of a mature protein sequence, such as from a structural gene, a linker sequence, or combinations thereof.

In preferred embodiments of the instant invention, the chimeric protein has a molecular weight of between about 400 to about 100,000 daltons or more (preferably between 1,000 and 50,000 daltons and can comprise any of the natural amino acids, such as Ala (A), Arg (R), Asp (D), Asn (N), Glu (E), Gin (O), Gly (G), His (H), Leu (L), Ile (I), Lys (K), Met (M), Cys (C), Phe (F), Pro (P), Ser (S), Thr (T), Trp (W), Tyr (Y), Val (V) (single letter amino acid code in parentheses), or may comprise any side chain-modified amino acid derivative commonly used in peptide chemistry. The latter amino acid derivatives include, for example, nipecotic acid, 1- or 2-napthylalanines and p-benzoylamino-L-phenylalanine, among others.

Inclusion bodies can be recovered from the host cells by known methods such as, for example, lysing the cells chemically or mechanically and separating the inclusion bodies (chimeric protein) by centrifugation.

During palladium promoted cleavage in accordance with the process of the instant invention, palladium ligands such as ethylenediamine, picolyl amine (2-aminomethylpyridine or "pic"), methionine, or histidine may be added to the reaction mixture to increase yield. Urea, preferably at a concentration of at least 4 M, may be added to the reaction mixture to increase the solubility of the chimeric protein. Cleavage is usually carried out at a temperature of between about 50° C. to about 70° C.

It is understood that the reaction conditions of the cleavage step of the process of the instant invention are adjusted depending on the palladium complex used and the characteristics of the polypeptide to be cleaved. The palladium complex should be solubilized, which will affect the reaction conditions. Moreover, in a preferred embodiment, the reaction conditions used will at least partially denature the polypeptide to be cleaved.

Palladium (Pd (II)) complexes that can promote the cleavage of polypeptides in accordance with the instant invention include $[Pd(OH_2)_3(OH)]^+$, $[PdCl_4]^{2-}$, cis-$[Pd(en)(OH_2)_2]^{2+}$, cis-$[Pd(pn)(OH_2)_2]^{2+}$, cis-$[Pd(pic)(OH_2)_2]^{2+}$, cis-$[Pd(bpy)(OH_2)_2]^{2+}$, cis-$[Pd(phen)(OH_2)_2]^{2+}$, and cis-$[Pd(dtco-OH)(OH_2)_2]^{2+}$. Additionally, Pd (IV) complexed with chloride ion as palladium hexachloride can also provide an effective cleavage agent. Pd complexes can be prepared by methods well known in the art (see e.g., (H. Hohmann et al., *Inorg. Chim. Acta*, 174: 87 (1990); T. Rau et al., *Inorg. Chem.*, 36: 1454 (1997); C. Drexler et al., *Inorg. Chem.*, 30: 1297 (1991), or U.S. Pat. No. 5,352,771) or can be purchased commercially. Preferred palladium complexes include salts of the following: $[PdCl_4]^{2-}$, $[Pd(NCCH_3)_2(OH_2)_2]^{2+}$, $[PdCl_6]^{2-}$, $[Pd(dppe)(OH_2)_2]^{2+}$, $[Pd(tpp)(OH_2)_2]^{2+}$, and $[Pd(dppf)(OH_2)_2]^{2+}$. Palladium complexes most preferred include $[PdCl_4]^{2-}$, $[Pd(NCCH_3)(OH_2)_2]^{2+}$, and $[PdCl_6]^2$. Complexes are used as the salt of an inorganic base, such as sodium or potassium. The sodium salt of $[PdCl_4]^{2-}$ is preferred.

In the process of the instant invention, cleavage of the chimeric protein at the Cys-His site occurs at the carboxamide bond between the histidine residue and the residue immediately adjacent to the histidine on the C-terminal side. For example, the protein $NH_2$-Ala-Ala-Cys-His-Gly-Gly-Gly-COOH (SEQ ID NO:6) would be cleaved as follows:

```
NH2-Ala-Ala-Cys-His-Gly-Gly-Gly-COOH
(SEQ ID NO: 6) + Palladium complex →
NH2-Ala-Ala-Cys-His-COOH(SEQ ID NO: 7)
```

(Polypeptides are designated herein by amino acid abbreviations and are written so that going from left to right the N-terminal amino acid is on the left and the C-terminal amino acid is on the right, e.g. $NH_2$-Ala-Ala-Cys-His-Gly-Gly-Gly-COOH (SEQ ID NO:6).)

The cleaved peptide produced in accordance with the process of the instant invention can be recovered from its fusion partner by ultrafiltration, precipitation, or more preferably, by ion-exchange chromatography. Any commercially available ion-exchange column suitable for the peptide being isolated may be employed. In many cases, the peptide recovered from the ion exchange column will refold into its native conformation, however, additional steps (e.g., oxidation) may be required to restore the peptide to a biologically active form, particularly when the peptide requires the formation of internal disulfide bonds for activity.

If desired, further purification steps can be employed using techniques known to those skilled in the art. Such steps may include, for example, HPLC, such as RP-HPLC or additional ion exchange chromatography steps.

In accordance with the process of the instant invention, the chimeric protein T7tag-Vg-$D_4$K-CH-GRF(1-44)-CH (SEQ ID NO:1) was recombinantly expressed in *E. Coli* and was thereafter recovered from the host cells in the form of an inclusion body. This chimeric protein has a leader sequence connected by a cystine (cys)-histidine (his) sequence to the growth hormone releasing factor peptide derivative GRF(1-44)-CH. T7tag-Vg-$D_4$K-CH-GRF(1-44)-CH (SEQ ID NO:1), comprised a 14-residue signal sequence followed by both a 27 residue vestigial (Vg) sequence (which induced inclusion body formation and high expression) and a 13-residue linker which contained the Cys-His cleavage site.

The isolated inclusion bodies were subjected to palladium-promoted acidic cleavage by solubilization in a reaction mixture comprised of (i) either 3 M citric acid, 3 M tartaric acid, 3 M maleic acid, 3 M to 6 M malonic acid, 3M malic acid, and 80% pyruvic acid, and (ii) tetrachloropalladate in a 10:1 molar ratio over chimeric protein (inclusion body). The cleavage reaction proceeded for between 1 to 24 hours, typically for about 1 to 6 hours, at a temperature ranging from about 50° C. to about 70° C. In some instances, ethylenediamine, picolyl amine (2-aminomethylpyridine or "pic"); methionine, or histidine were added to the reaction mixture to increase yield.

Under these conditions, yields of cleaved peptide in the range of around 30% (using 3 M tartaric acid) to around 50% (using 5 M malonic acid) were obtained in as short a time as 2 hours. rGRF(1-44)-CH was produced by a preferred embodiment of the instant invention which reacted the inclusion body (chimeric protein) with 5 M malonic acid and tetrachloropalladate in the cleavage step (with a 10:1 molar ratio of tetrachloropalladate to inclusion body (chimeric protein)) for around 90 minutes to yield around 45% cleaved protein, which was thereafter purified by HPLC.

In another embodiment of the instant invention, DNA encoding PTH(1-34) was cloned downstream of a leader sequence in a bacterial expression vector and was expressed in *E. Coli* to generate the chimeric protein T7tag-Vg-$G_5$PR-CH-PTH(1-34) (SEQ ID NO:3). This chimeric protein was recovered from the host cells as an inclusion body and was subjected to palladium-promoted acidic cleavage in a reaction mixture comprising 3 M citric acid, sodium tetrachloropalladate and either pic, methionine or histidine. This reaction yielded almost 100% cleaved rPTH(1-34) in 2 hours or less.

In still another embodiment of the instant invention, DNA encoding PTH(1-84) was cloned downstream of a leader sequence in a bacterial expression vector and was expressed in *E. Coli* to generate the chimeric protein T7tag-Vg-G5PR-CH-PTH(1-84) (SEQ ID NO:4). This chimeric protein was recovered from the host cells in the form of an inclusion body and was subjected to palladium-promoted acidic cleavage in reaction mixtures comprising either 3 M citric acid or 5 M malonic acid. Ethylenediamine (5.2 mM) and tetrachloropalladate (2.6 mM) were added to each of these two cleavage sample solutions, and the cleavage reaction proceeded at 60° C. for four hours and yielded approximately 50% cleaved rPTH(1-84) as determined by HPLC.

Other embodiments of the instant invention are disclosed in the following Examples, which are illustrative and not limiting. The examples provided are to disclose techniques used in general, with specific uses illustrated for palladate promoted cleavages of T7tag-Vg-$D_4$K-CH-GRF(1-44)-A (SEQ ID NO:2), T7tag-Vg-$D_4$K-CH-GRF(1-44)-CH (SEQ ID NO:1), T7tag-Vg-$G_5$PR-CH-PTH(1-34) (SEQ ID NO:3), and T7tag-Vg-$G_5$PR-CH-PTH (1-84) (SEQ ID NO:4).

EXAMPLE 1

Expression of the T7tag-Vg-D$_4$K-CH-GRF(1-44)-CH (SEQ ID NO:1) Precursor Peptide T7tag-Vg-D$_4$K-CH-GRF(1-44)-CH (SEQ ID NO:1) was recombinantly expressed in *E. Coli* as follows. *E. Coli* bacteria containing the expression plasmid encoding the leader-CH-GRF(1-44)CH (SEQ ID NO:21) polypeptide (FIG. 7) were grown in 500 mL shake flasks containing tryptone, yeast, glucose, batch salts (sodium and potassium mono- and diphosphate salts and ammonium sulfate), and antibiotic. Inoculated shake flasks were subject to orbital shaking (200 rpm, 37° C.). Incubation was completed when the culture reached an optical density (OD) of 0.8-1.8 at 540 nm.

Fermenters ranging from 5 L to 100 L production capacities were seeded using shake flask cultures. The media included batch salts, glucose, and chelated metals solution (potassium citrate, sodium citrate, magnesium sulfate, phosphoric acid ferric chloride, zinc chloride, cobalt chloride, sodium molybdate, manganese chloride, calcium chloride, and copper sulfate). The pH of the medium was adjusted to 6.9 prior to inoculation and the pH was maintained at 6.9 during culture. Dissolved oxygen was maintained at approximately 40%, via agitation and supplemental oxygen. Either silicone-based or polypropylene glycol-based "antifoam" was added aseptically on an "as needed" basis to reduce foaming in the fermentation culture.

When the fermentation culture OD reached 25 at 540 nm, recombinant protein expression was induced by adding filter-sterilized isopropylthiogalactoside (IPTG, 600 mM) to a final concentration of 0.5 mM, followed by filter-sterilized magnesium induction supplement (potassium citrate and magnesium sulfate). The culture was incubated for another 6 hr, and then cooled to 10-15° C.

EXAMPLE 2

Isolation of Inclusion Body T7tag-Vg-D$_4$K-CH-GRF(1-441-CH (SEQ ID NO:1) Precursor Peptide Production fermenter cells were harvested from the fermentation broth by centrifugation. Cell pellets were pooled, resuspended in an appropriate volume (for example, 2 L lysis buffer for material from a 5 L fermentor) of lysis buffer (6g Tris free base and 0.93 g EDTA in 993 g water), and lysed in a high-pressure homogenizer.

Cell solids and peptide precursor-containing inclusion bodies were pelleted by centrifugation, collected, and dissolved via homogenization in 1.5 M citric acid/1.0 mM EDTA solution, at a pH of approximately 1.0 (for example, 1.5 L solution for material from a 5 L fermentor). The pH of this suspension was adjusted to 4.9 by slow addition of 10 M sodium hydroxide with continuous mixing, while maintaining the temperature at less than 15° C. The precipitate containing the GRF precursor peptide was collected by centrifugation and washed twice by resuspending in water and centrifuging to a pellet.

EXAMPLE 3

Preparation of Palladate Cleavage Promoters

The following chemical abbreviations are used herein: en=ethylenediamine; pic=picolyl amine (or 2-aminomethylpyridine); aep=2(2-aminoethyl)pyridine; dien=diethylenetriamine.

Na$_2$PdCl$_4$ and K$_2$PdCl$_4$ were purchased from Aldrich Chemical Co. and Stem Chemical Co.

Solid samples of tetrachloropalladate were solubilized in an appropriate aqueous solvent to a concentration of about 250 mM. Aliquots were then diluted into reaction mixtures to the appropriate concentrations. The solvents were chosen to be the same as the acid solution of the reaction under investigation.

EXAMPLE 4

Analytical Methods

The following analytical methods and devices were used.
HPLC Method 1:
Reversed phase chromatography on a Microsorb-MY Cyano-C$_8$ 100 Å, 5 μm, 4.6×150 mm column (Catalog #R0086800D5). The mobile phase system was as follows: A=5% (v/v) acetonitrile, 0.1% (v/v) trifluoroacetic acid; B=95% (v/v) acetonitrile, 0.1% (v/v) trifluoroacetic acid. The gradient used to quantitate the inclusion body sample, (t=0 hours) was as follows: 10-100% B (10.8 min.), 100% B (0.6 min.), 100-10% B (0.6 min.) at 1 mL/min at ambient temperature. The gradient for analysis of the quenched reactions was as follows: 20-30% B (3 min.), 30-40% B (6 min.), 40-100% B (1.5 min), 100-20% B (0.6 min.), 20% B (3 min.) at 1 mL/min at 30° C. Absorbance was monitored from 210-320 nm.
HPLC Method 2:
Reversed phase HPLC used a Waters Symmetry C$_{18}$, 100 Å, 3.5 μm, 4.6×150 mm column. The mobile phase system was as follows: A=5% (v/v) acetonitrile, 0.1% (v/v) trifluoroacetic acid; B=95% (v/v) acetonitrile, 0.1% (v/v) trifluoroacetic acid. The gradient was 25-33% B (24 min.), 33-60% B (6 min.), 60-90% B (1 min.), 90-25% B (0.5 min.), 25% B (4 min.) at 1 mL/min and 40° C. The absorbance was monitored from 210-320 nm.
HPLC Method 3:
The LC/MS method utilized a Waters Symmetry C$_{18}$ column, 100 Å, 3.55 μm, 2.1×150 mm column. The mobile phase system was as follows: A=10% (v/v) acetonitrile, 0.1% (v/v) trifluoroacetic acid; B=60% (v/v) acetonitrile, 0.1% (v/v) trifluoroacetic acid. The gradient was 20-30% B (1 min.), 30-50% B (25 min.), 50-100% B (4 min.), 100-20% B (1 min.), 20% B (7 min.) at 0.25 mL/min at 40° C. The absorbance was monitored from 210-320 nm. The LCQ Duo MS detector was set to source from 7-19 min. and 24-30 min. The scan event was set from 700-2000 m/z units.

All the reverse-phase HPLC data was collected on a Beckman System Gold HPLC with a photo diode array detector. The LC/MS data was collected on a ThermoQuest Surveyor HPLC with a photo diode array detector and a ThermoQuest Finnigan LCQDuo mass detector.

Palladium complex cleavage reaction conditions cause the binding of palladium to GRF and PTH derivatives, in complexes tight enough to survive analytical HPLC conditions. Therefore the GRF-A-derived samples were diluted 10 fold into urea/Tricarboxyethylphosphine (TCEP) for a final concentration of 6.8 M urea and 5 mM TCEP prior to injection, which resulted the removal of the tightly bound palladium.

Alternatively, the same effect could be achieved by diluting 6-fold into a solution, with final concentrations of 20 mM thiourea and 200 mM HCl. Alternatively, the same effect was achieved by diluting 4-fold into 0.4 M NaCl, and centrifuging the precipitate before injecting the sample into the HPLC. The GRF(1-44)-CH analytical samples were treated as described below. The PTH(1-34) samples were treated by dilution by six-fold dilution into 0.25 M HCl and 25 mM thiourea. The PTH(1-84) samples were diluted 10 fold into a final concentration of 20 mM thiourea, and 7 M urea.

During the optimization of the palladate cleavage of T7tag-Vg-D$_4$K-CH-GRF(1-44)-CH (SEQ ID NO:1), it was discovered that the palladium was binding tightly to the C-terminal CH site. This Pd-GRF complex had an altered spectrum, which inflated the peak area and in turn inflated the cleavage yields. A treatment method for preparing the samples, referred to as the dtc treatment, was developed. The treatment was as follows: 50 µL of sample was added to 425 µL of 20 mM sodium diethyldithiocarbamate (ddtc) in 8 M urea and allowed to stand at room temperature for five minutes. After the incubation, 25 µL of 100 mM TCEP was added and the sample was centrifuged to remove the yellow palladate precipitate.

EXAMPLE 5

Pd-Promoted Hydrolytic Cleavage of T7tag-Vg-D$_4$K-CH-GRF(1-44)-Ala (SEQ ID NO:2) in Citric Acid T7tag-Vg-D$_4$K-CH-GRF(1-44)-Ala (SEQ ID NO:2) precursor peptide (FIG. 6) was prepared by the methodology described in Example 1, inclusion bodies were isolated as in Example 2, and 1 g (wet weight) of the inclusion bodies solubilized in 50 mL of 3 M citric acid (peptide concentration 3 mg/mL). The solution was divided in two equal parts, and to each tetrachloropalladate was added to a concentration of 5.56 mM. One solution received an additional 11 mM ethylenediamine. The solutions were incubated at 60° C. for 5 hours, and aliquots removed every hour, for quenching and analysis by HPLC, using method 1 of Example 4. The results are reported as percentage of the maximum theoretically expected yield of GRF(1-44)-Ala, in Table 1

TABLE 1

Time course of the reaction of tetrachloropalladate with T7tag-Vg-D$_4$K-CH-GRF(1-44)-Ala (SEQ ID NO: 2) in citric acid, with and without ethylenediamine.

| Time of reaction (hrs) | % Product (GRF(1-44)-Ala) formed in 3 M citric acid | % Product (GRF(1-44)-Ala) formed in 3 M citric acid, 11 mM ethylenediamine |
|---|---|---|
| 1 | 26.2 | 31.5 |
| 2 | Not analyzed | 50.1 |
| 3 | 52.2 | 62.4 |
| 4 | 54.8 | 70.1 |
| 5 | 59.7 | 73.8 |

The higher yield of the ethylenediamine treated reaction mixture shows that ethylenediamine acts to increase the attainable yield of GRF(1-44)-Ala during palladate-promoted cleavage of T7tag-Vg-D$_4$K-CH-GRF(1-44)-Ala (SEQ ID NO:2).

EXAMPLE 6

Figure 2:
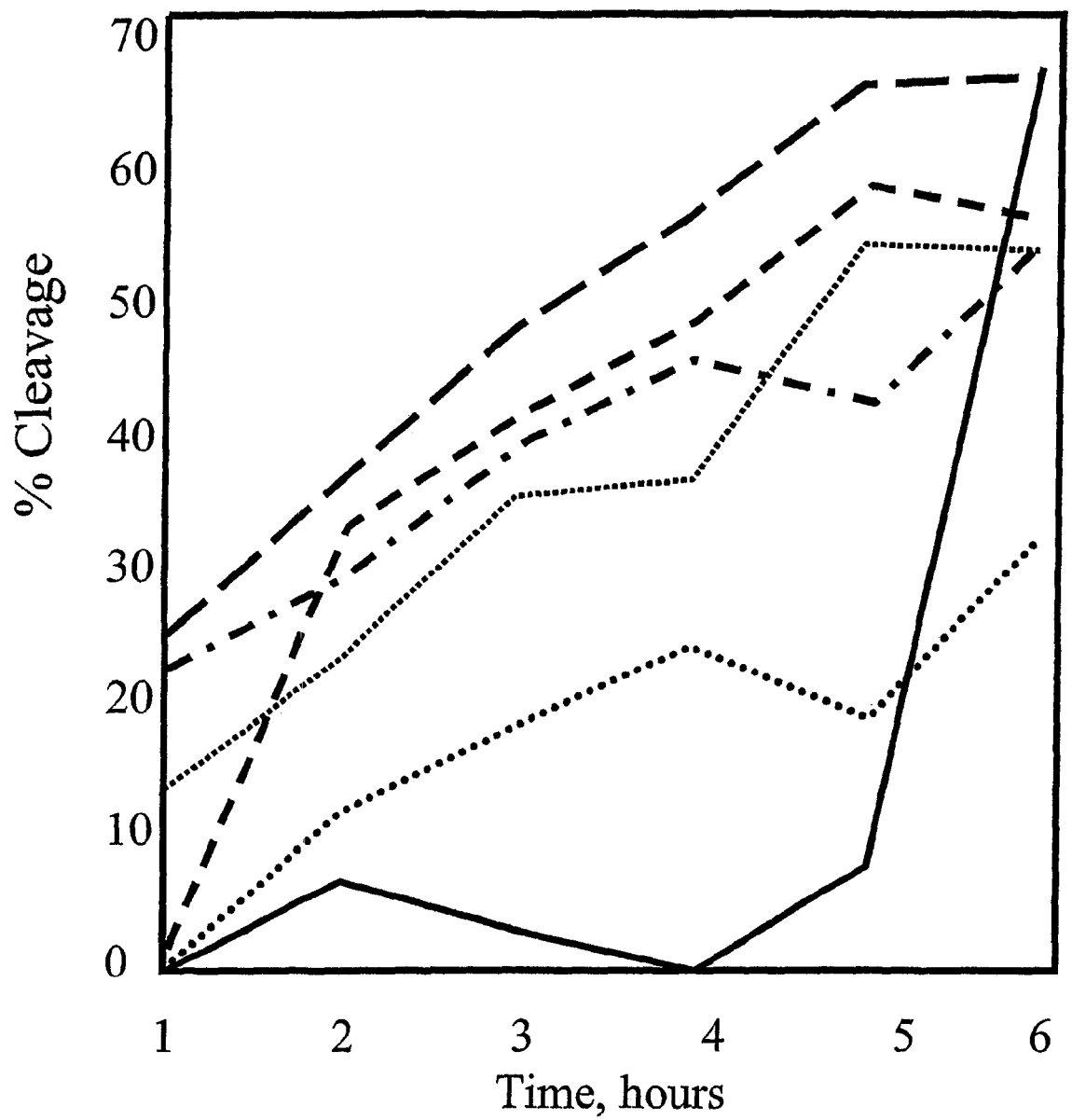
FIG. 2 illustrates tetrachloropalladate cleavage of T7tag-$D_4$K-CH-GRF(1-44)-CH (SEQ ID NO:5) in various organic acids in the presence of ethylenediamine over the course of 6 hours in accordance with the process of the instant invention. The various acids are as follows: Malonic (long dashes), Tartaric (circular dots), Pyruvic (alternating dashes), Citric (short dashes), Malic (square dashes), and Maleic (solid line).

Tetrachloropalladate promoted hydrolytic cleavage of T7tag-Vg-D$_4$K-CH-GRF(1-44)-CH (SEQ ID NO:1) in 3 M citric, 3 M tartaric, 3 M maleic, 3 M malonic, 3 M maleic, and 80% pyruvic acids The solubilization and cleavage of T7tag-Vg-D$_4$K-CH-GRF(1-44)-CH (SEQ ID NO:1) in 3 M citric, 3 M tartaric, 3 M maleic, 3 M malonic, 3 M malic, and 80% pyruvic acids were studied. Each acid was investigated with and without ethylenediamine. For each acid, the precursor peptide was homogenized using the plastic probe and the OMNI 5000 high-sheer homogenizer, aiming for ~5 mg/mL or 0.45 mM precursor peptide. After solubilization, a sample of each solution was taken as a t=0 hr time point which was used to determine the 100% theoretical cleavage yield and to examine the solubility of the construct in each individual acid. The tetrachloropalladate was added at a 5 molar excess per Cys-His, or 4.5 mM. In the reactions where ethylenediamine was present, it was added in a 2:1 ratio over palladium. The reactions were done at 60° C. for six hours, with time points taken every hour. The time points were diluted six-fold with 48 mM thiourea (40 mM final thiourea). All analytical analyses were done as described using method 1, Example 4. The results of these studies (FIG. 1) shows that in all cases cleavage occurs in a time dependent manner with maximal yield of about 63% being achieved with malonic acid in about 3 hours. Reaction in maleic acid was very slow. With ethylenediamine present (FIG. 2) the reactions are generally slower but reached a higher yield, that of malonic being about 68% after 6 hours. Ethylenediamine however does result in effective cleavage with maleic acid after 6 hours.

EXAMPLE 7

Figure 3:
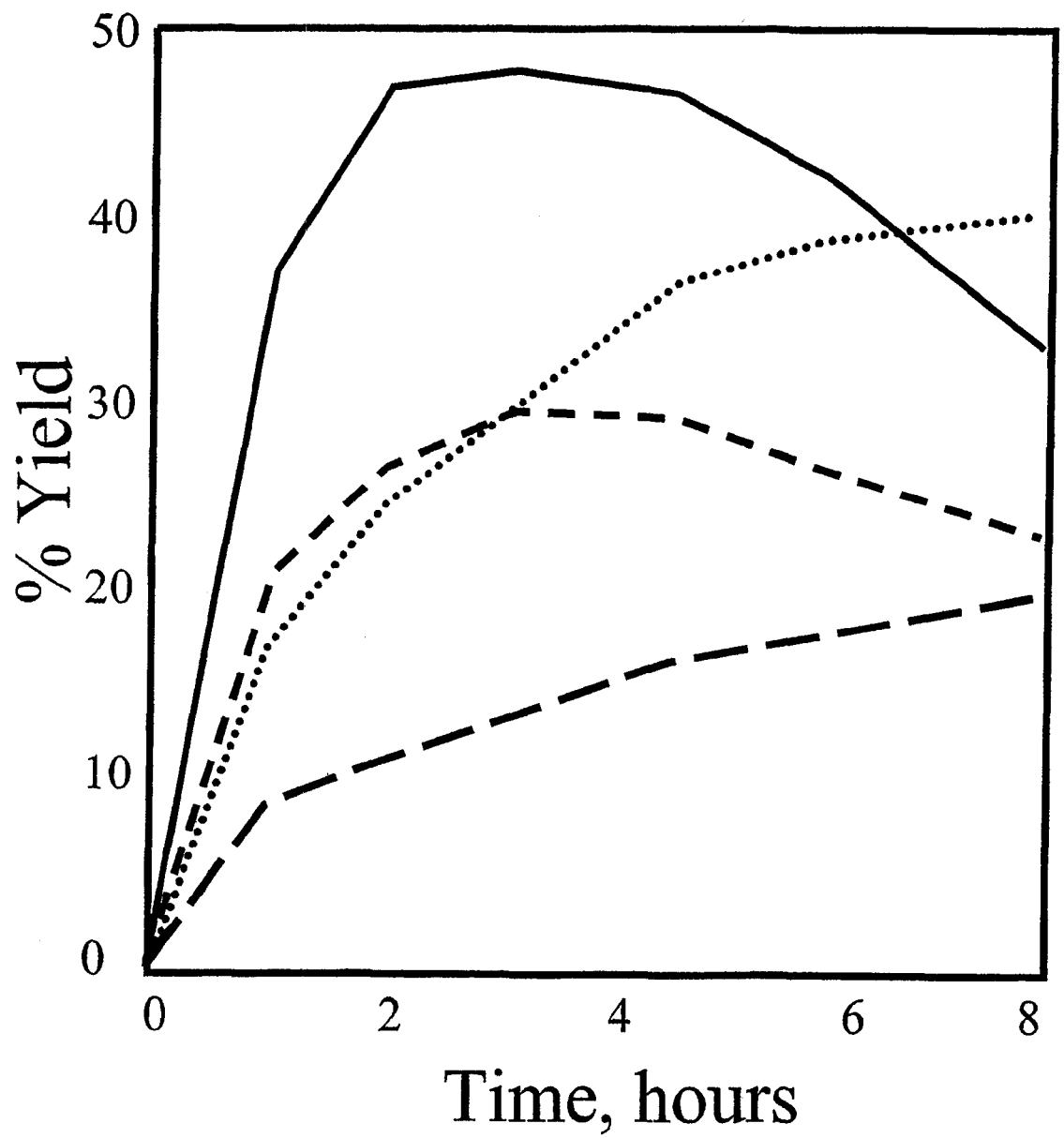
FIG. 3 illustrates cleavage yield of T7tag-$D_4$K-CH-GRF (1-44)-CH (SEQ ID NO:5) in malonic and tartaric acids at different temperatures in accordance with the process of the instant invention. Solid line: malonic acid at 60° C., dotted line: malonic acid at 50° C., dashed line: tartaric acid at 50° C., large dashed line: tartaric acid at 50° C.

The Effect of Temperature on the Tetrachloropalladate Promoted Hydrolytic Cleavage of T7tag-Vg-D$_4$K-CH-GRF(1-44)-CH (SEQ ID NO:1) in Malonic, and Tartaric Acids An experimental matrix was designed to further investigate tetrachloropalladate cleavage in malonic and tartaric acids. The matrix was prepared as follows: 5 M malonic acid with 4 mM tetrachloropalladate, each at 50 and 60° C. For 3 M tartaric acid, 4 mM tetrachloropalladate was used. The samples were ddtc-treated and analyzed with methods 2 and 3, example 4. FIG. 3 shows that compared to 50° C. the 60° C. samples cleaved considerably faster. Malonic acid reached a maximum cleavage yield in less than two hours of about 55%. Similar results are found for tartaric acid but the yields are considerably lower. At lower temperatures the reactions were slow such as to be impractical for achieving effective yields.

EXAMPLE 8

Optimization of Tetrachloropalladate and Malonic Acid Concentrations for the Cleavage (SEQ ID NO:1) in Malonic Acid.

Figure 4:
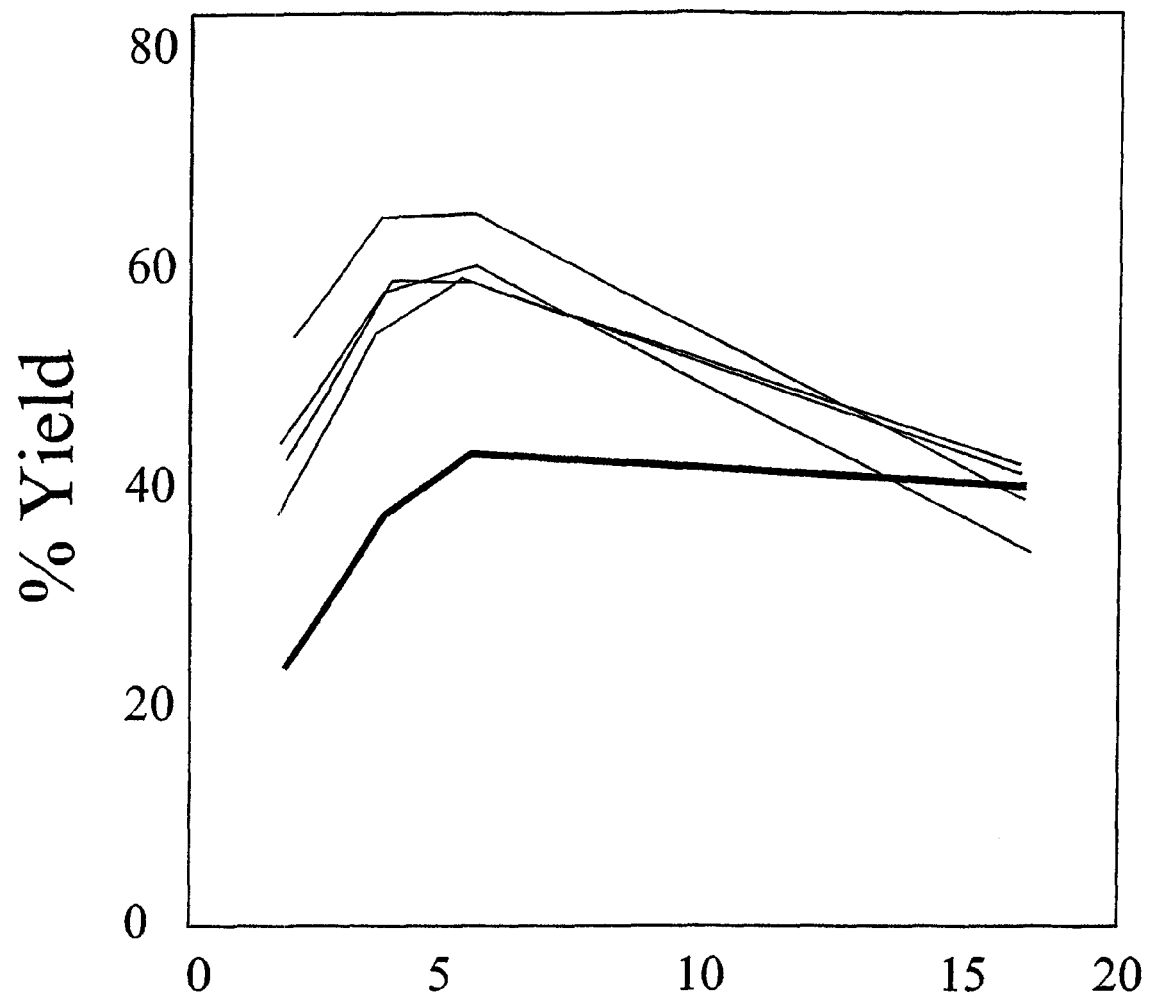
FIG. 4 illustrates the cleavage of T7tag-$D_4$K-CH-GRF(1-44)-CH (SEQ ID NO:5) as a function of malonic acid concentration in accordance with the process of the instant invention. The acid concentration was 2, 3, 4, 5, and 6 molar from the lower curve to the upper curve respectively.
Figure 5:
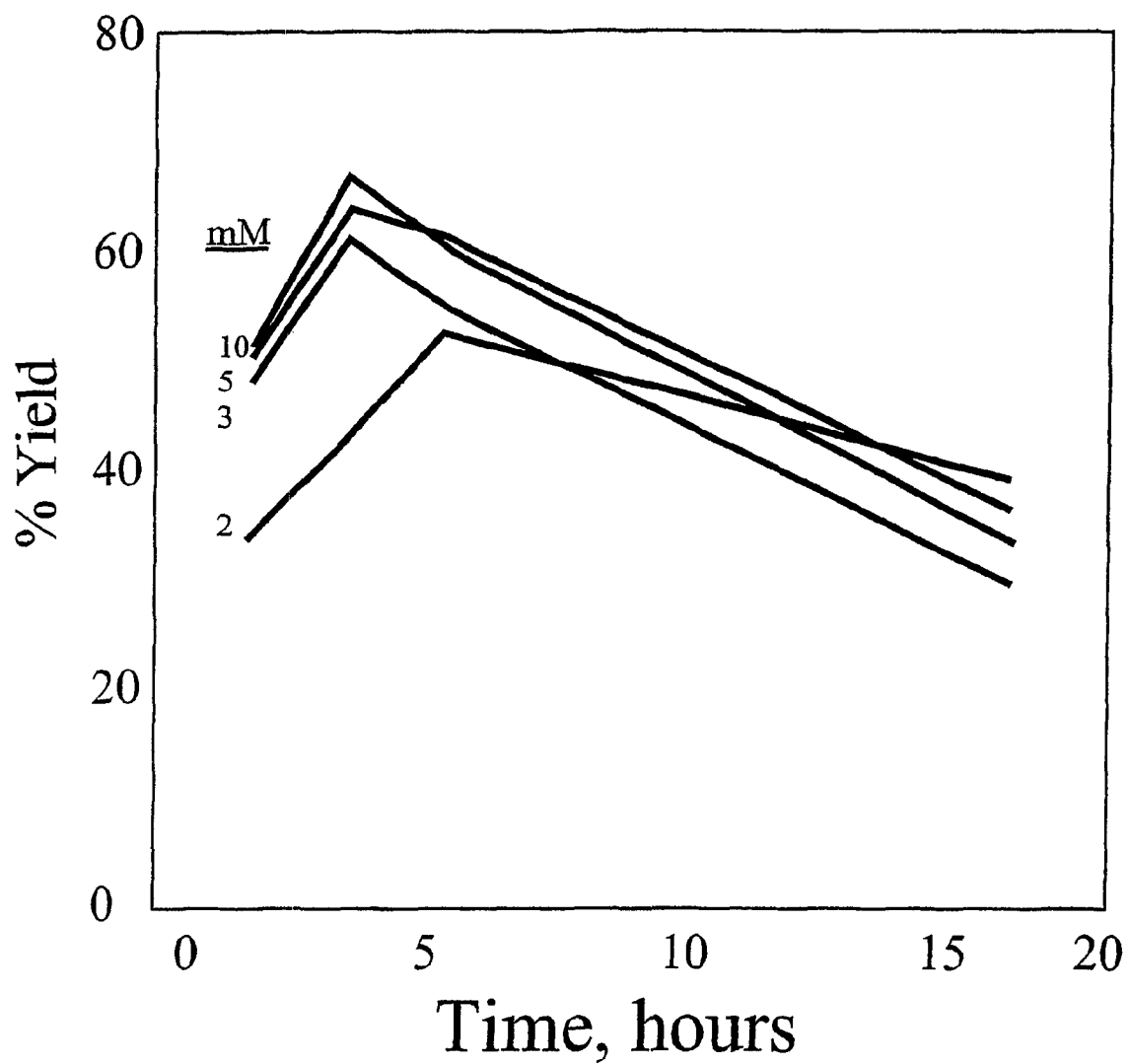
FIG. 5 illustrates the cleavage of T7tag-$D_4$K-CH-GRF(1-44)-CH (SEQ ID NO:5) as a function of tetrachloropalladate concentration in accordance with the process of the instant invention. The tetrachloropalladate concentration was 2, 3, 5, and 10 mM from the lower curve to the upper curve.

A matrix was designed to determine the effects of the concentrations of both malonic acid and tetrachloropalladate. Each reaction was done at approximately 5 mg/mL construct. The malonic series contained 2, 3, 4, 5, and 6 M malonic acid with 5 mM tetrachloropalladate and 10 mM ethylenediamine. The second series was done in 6 M malonic acid with 2, 3, 5, and 10 mM tetrachloropalladate with 4, 6, 10, and 20 mM ethylenediamine respectively. The reactions were conducted at 60° C. with time points taken at 2, 4, 6, and 18 hours. Each time point was diluted ten-fold with 8 M urea, 20 mM ddtc, and TCEP The analysis used method 1, Example 4. FIG. 4 shows that the optimal malonic acid concentration is 5 M and FIG. 5 shows that 3 to 5 mM tetrachloropalladate are equivalent and provide high yields.

EXAMPLE 9

Production of T7tag-Vg-G$_5$PR-CH-PTH(1-34) (SEQ ID NO:3)

DNA encoding PTH(1-34) was cloned downstream of a leader sequence T7tag-Vg-G$_5$PR (SEQ ID NO:8) in a bacterial expression vector to generate T7tag-Vg-G$_5$PR-CH-PTH(1-34) (SEQ ID NO:3) (FIG. 8), using the techniques described in Example 1. Inclusion body preparations were obtained from *E. coli* transformed with the expression construct essentially as described above for the production of GRF(1-44)-CH in Example 2. Precipitated inclusion bodies were washed by resuspension in water with sonication, and centrifuged to obtain a pellet.

EXAMPLE 10

Cleavage of T7tag-Vg-G$_4$PR-CH-PTH(1-34) (SEQ ID NO:3) by Tetrachloropalladate The pellet from Example 9 was dissolved at a concentration of 6 mg/mL in the citric acid and palladate complex mixtures, as indicted in Table 1.

The solution was incubated at a temperature between 60° C. and 70° C. for the time indicated in Table 2. As indicated below, the reactions also included addition of agents at about a 2-fold molar excess over tetrachloropalladate, to determine whether they might influence the yield of the product PTH(1-34). After the specified incubation period, the reaction was diluted 1:10 in 0.2 mM HCl and stored at room temperature for 16 hr. The mixture was then treated with 2 mM potassium thiocyanate to precipitate unreacted Pd complexes and inclusion bodies.

HPLC was used to measure the amount of PTH(1-34) cleaved from the chimeric protein during the reaction. The post-treated material was loaded on a Phenomenex 5 micron C18 reversed-phase analytical column in Buffer A (5% acetonitrile in water, containing 0.1% TFA). Column elution was effected with linear gradients of Buffer B (95% acetonitrile in 0.1% TFA) in Buffer A (rising to 30% B in 4 min, hold at 30% B for 4 min, to 50% B at 33 min, then to 100% B at 35 min.). Two major peptide-containing peaks were obtained: one at 15.4 and the other at 16.6 min. The MALDI-TOF mass spectrum of the 15.4 min peak gave a single peak at 4119, indicating the peak to have a mass identical to that of PTH(1-34). Reference standard PTH(1-34) also gave a single 15.4 min peak on HPLC analysis, indicating that the 15.4 min peak from the cleaved material was PTH(1-34). The overall results of tetrachloropalladate-promoted cleavage of PTH(1-34) are shown in Table 2.

TABLE 2

Yield of PTH (1-34) by tetrachloropalladate-Promoted Cleavage of T7tag-Vg-G$_5$PR-CH-PTH(1-34) (SEQ ID NO: 3).

| Pd(II) complexes | Medium | Temp. (° C.) | Time (hr) | Yield (%) |
|---|---|---|---|---|
| Na$_2$PdCl$_4$ | 2.55 M citric acid | 60 | 2 | No product |
| Na$_2$PdCl$_4$ + histidine | 2.55 M citric acid | 60 | 2 | ≈100 |
| Na$_2$PdCl$_4$ + en | 3.2 M citric acid | 60 | 2 | 44 |
| Na$_2$PdCl$_4$ + pic | 3.2 M citric acid | 60 | 2 | ≈100 |
| Na$_2$PdCl$_4$ + aep | 3.2 M citric acid | 60 | 2 | 68 |
| Na$_2$PdCl$_4$ + D/L-methionine | 3.2 M citric acid | 60 | 2 | ≈100 |
| Na$_2$PdCl$_4$ + cysteine | 3.2 M citric acid | 60 | 2 | 79 |
| Na$_2$PdCl$_4$ + imidazole | 3.2 M citric acid | 60 | 2 | 8 |
| Na$_2$PdCl$_4$ + histidine | 3.2 M citric acid | 66 | 3 | 93 |
| Na$_2$PdCl$_4$ + histidine | 3.2 M citric acid | 70 | 1.5 | 90 |
| Na$_2$PdCl$_4$ + dien | 3.2 M citric acid | 66 | 2 | 85 |
| Na$_2$PdCl$_4$ + en | 3.2 M citric acid | 66 | 2 | >90 |

These results show rapid and high yield cleavage of PTH (1-34) from chimeric protein-containing inclusion bodies incubated at 60-70° C. in high concentrations of citric acid with sodium tetrachloropalladate OD; in the presence of pic, D/L methionine or histidine, almost 100% cleavage of native PTH(1-34) was obtained in 2 hr or less.

EXAMPLE 11

Production of T7tag-Vg-G5PR-CH-PTH(1-84) (SEQ ID NO:4)

DNA encoding PTH(1-84) was cloned downstream of a leader sequence T7tag-Vg-G5PR (SEQ ID NO:8) in a bacterial expression vector to generate of T7tag-Vg-G5PR-CH-PTH(1-84) (SEQ ID NO:4) (FIG. 9), using the techniques disclosed in Example 1. Whole cell preparations were obtained from *E. coli* transformed with the expression construct essentially as described above for the production of GRF(1-44)-CH in Example 1. Whole cells were collected by centrifugation and stored frozen. The precursor peptide was distributed between inclusion bodies and the supernatant fluid when small aliquots were examined by breaking the cells by sonication.

Approximately 1 g aliquots of a whole cell paste made from T7tag-Vg-G5PR-CH-PTH(1-84) (SEQ ID NO:4) inclusion bodies were dissolved in a 20 mL of 3 M citric acid and 20 mL of 5 M malonic acid. Both solutions were clarified by centrifugation. The centrifugation supernatants from both centrifuged solutions were split into two samples. Each of the resulting four solutions contained about 2 mg/mL of inclusion bodies; ethylenediamine was added to one citric acid and one malonic acid samples at a concentration of 5.2 mM to make two cleavage samples. Tetrachloropalladate (2.6 mM) was added to each of the four cleavage samples, and the cleavage samples were kept at 60° C. for four hours. Samples were withdrawn from each of the two cleavage samples and assayed qualitatively by LC-MS and by PAGE. The two cleavage samples were treated with tricarboxyethyl phosphine in urea to remove palladate and the samples were then analyzed by method 3, Example 4.

Figure 10:
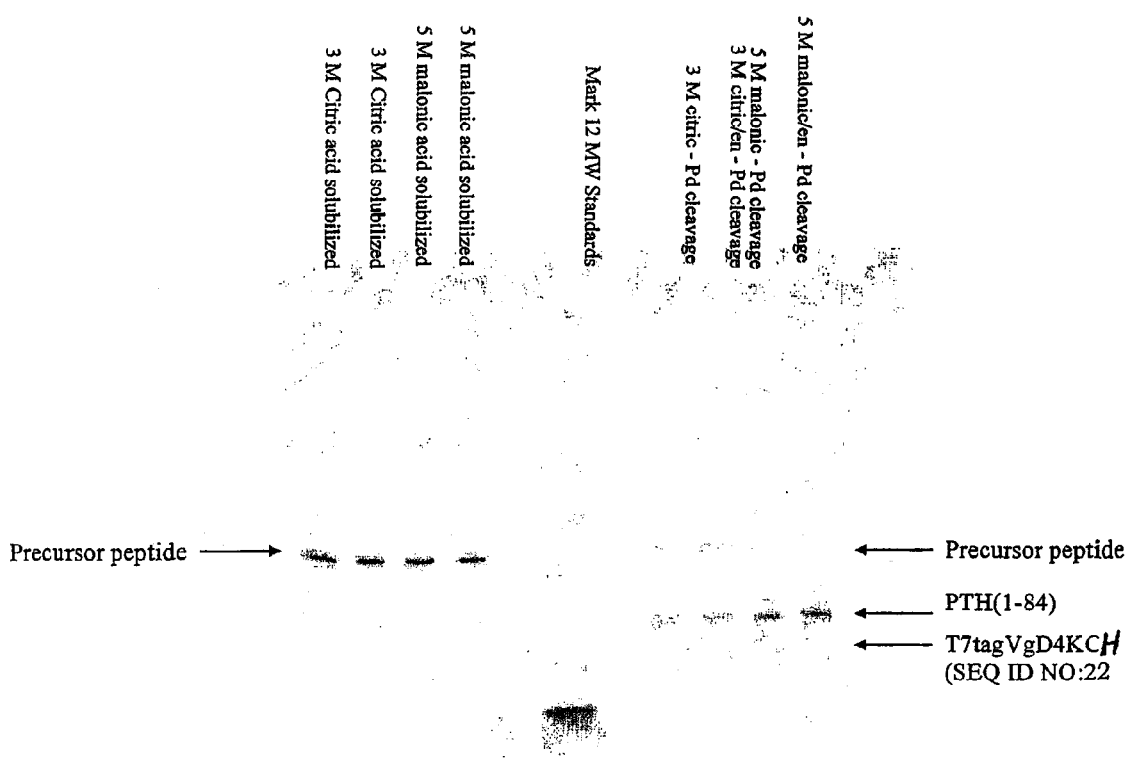
FIG. 10 illustrates the cleavage of T7tagVgG5PRCH-PTH (1-84) (SEQ ID NO:4) in citric and malonic acids in accordance with the process of the instant invention. The arrows indicate the position of: T7tagVgG5PRCH-PTH(1-84) (SEQ ID NO:4) precursor peptide, PTH(1-84), and T7tagVgG5PRCH-PTH(1-84).

By four hours, cleavage reactions were complete in both samples and production of PTH(1-84) (identity confirmed by the mass spectra) at about 50% yield was observed. FIG. 10 illustrates the extent of cleavage achieved, as determined by gel electrophoresis analysis.

All publications, patents and patent applications and priority U.S. patent application Ser. No. 60/383,488, filed 24 May 2003, are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A palladium complex-promoted hydrolytic polypeptide cleavage process which selectively cleaves a polypeptide at a Cys-His cleavage site, comprising:
   solubilizing the polypeptide in a reaction mixture comprised of a palladium complex dissolved in a high-concentration organic acid solvent selected from the group consisting of acetic acid, propionic acid, butyric acid, pyruvic acid, lactic acid, tartaric acid, citric acid, oxalic acid, malic acid, maleic acid, malonic acid, fumaric acid, glutaric acid, adipoc acid, succinic acid, pimelic acid, tricarballylic acid, glucuronic acid, saccharic acid, and dicarboxylic acids,
   wherein the concentration of the organic solvent in the reaction mixture is from about 1 to about 22 molar, and
   wherein the cleavage occurs at the carboxamide bond between the histidine residue and the residue immediately adjacent to the histidine on the C-terminal side.

2. The process of claim 1, wherein the polypeptide is a recombinantly expressed chimeric protein in the form of an inclusion body and the molar ratio of palladium complex to inclusion body in the reaction mixture is from about 2:1 to about 20:1.

3. The process of claim 2, wherein the chimeric protein cleavage site includes a linker, which is adjacent to Cys.

4. The process of claim 3, wherein the linker is selected from the group consisting of DDDD (SEQ ID NO:9), DDDK (SEQ ID NO:10), DTRL (SEQ ID NO:11), and GGPR (SEQ ID NO:12).

5. The process of claim 1, wherein the reaction mixture temperature is maintained at about 50° C. to about 70° C.

6. The process of claim 1, wherein the cleavage reaction proceeds for 1 to 6 hours.

7. The process of claim 1, wherein the organic acid solvent is combined with one or more palladium complexes with ligands selected from the group consisting of ethylenediamine; propylenediamine; 2-aminomethyl pyridine; 2(2-aminoethyl) pyridine; 2(2-methylaminoethyl)pyridine; 2,2'-bypyridyl; 1,10-phenanthroline: 3-hydroxy-2 (dimethylaminomethyl)pyridine; 3-hydroxy-1,5-dithiacyclooctane; 3,6-dithiaoctane-1,8-diol; 1,2-diphenylphosphineethane; triphenylphosphine; diphenylphosphineferrocene; and diethylenetriamine.

8. The process of claim 1, wherein the palladium promoter is a Palladium(II) complex selected from the group consisting of $Na_2PdCl_4$; cis-[Pd(en)$Cl_2$]; cis-[Pd(bp)$Cl_2$]; cis-[Pd(phen)$Cl_2$]; cis-[Pd(pn)$Cl_2$]; cis-[Pd(pic)$Cl_2$]; cis-[Pd(dtco-OH)$Cl_2$cis-[Pd(en)(OH$_2$)$_2$]$^{2+}$, cis-[Pd(pn)(OH$_2$)$_2$]$^{2+}$, cis-[Pd(pic)(OH$_2$)$_2$]$^{2+}$, cis-[Pd(bp)(OH$_2$)$_2$]$^{2+}$; cis-[Pd(phen)(OH$_2$)$_2$]$^{2+}$; cis-(Pd(dtco-OH)(OH$_2$)$_2$]$^{2+}$; and [Pd(OH$_2$)$_3$(OH)](NO$_3$).

9. The process of claims 1, wherein the palladium complex is tetrachloropalladate and the molar ratio of tetrachloropalladate to polypeptide is around 10:1.

10. The process of claim 1, wherein the organic solvent is combined with an inorganic acid selected from the group consisting of HCl, $H_3PO_4$, $H_2SO_4$, or $HClO_4$.

11. The process of claim 1, wherein the organic acid solvent is selected from the group consisting of acetic acid, propionic acid, butyric acid, pyruvic acid, lactic acid, tartaric acid, citric acid, oxalic acid, malic acid, maleic acid, malonic acid, fumaric acid, glutaric acid, adipoc acid, succinic acid, pimelic acid, tricarballylic acid, glucuronic acid, and saccharic acid.

12. The process of claim 1, wherein the organic solvent is malonic acid.

13. The process of claim 1, wherein the organic solvent is 5 M malonic acid or 6 M malonic acid, and the palladium complex is tetrachloropalladate.

14. The process of claim 1, wherein the organic solvent is citric acid.

15. The process of claim 1, wherein the organic solvent is 3 M citric acid, the palladium complex is sodium tetrachloropalladate, and the reaction mixture comprises a palladate ligand selected from the group consisting of pic, methionine or histidine.

16. The process of claim 1, wherein the polypeptide, which comprises the Cys-His cleavage site, is a glucagon-like peptide-1 (GLP-1), a glucagon-like peptide-2 (GLP-2), a parathyroid hormone (PTH), a growth hormone releasing hormone (GRF), a parathyroid hormone related protein, an adrenocorticotropic hormone (ACTH), an enkephalin, an endorphin, an exendin, an amylin, an opioid peptide, a gaegurin 5, a gaegurin 6, a brevinin 1, a ranatuerin selected from the group consisting of ranatuerin 1 through 9, an esculetin, a glucose-dependent insulinotropic polypeptide (GIP), a glucagon, a motilin, a thymopoietin, a thymosin, an ubiquitin, a serum thymic factor, a thymic humoral factor, a neurotensin, a tuftsin, a gastrin, a calcitonin, a luteinizing-hormone-releasing hormone, a pancreatic polypeptide, an endothelin, a corticotrophin releasing factor, a neuropeptide Y, an atrial naturetic peptide, a galanin, a somatostatin, a vasoactive intestinal peptide, or an insulin.

17. The process of claim 16, wherein the polypeptide is made synthetically.

18. The process of claims 16, wherein the polypeptide was expressed recombinantly in host cells and was recovered from the host cells in the form of an inclusion body.

19. The process of claim 18, wherein the host cells are *Escherichia coli*.

20. A peptide purification process comprising:
(a) cleaving the polypeptide of the process of claim 1; and
(b) recovering the cleaved polypeptide from step (a) by ultrafiltration, filtration or ion-exchange chromatography.

* * * * *

SEQUENCE LISTING

<160> NUMBER OF SEQ ID NOS: 22

<210> SEQ ID NO 1
<211> LENGTH: 91
<212> TYPE: PRT
<213> ORGANISM: Artificial Sequence
<220> FEATURE:
<223> OTHER INFORMATION: polypeptide

<400> SEQUENCE: 1

Arg Gly Ser Gly Gln Gly Gln Ala Gln Tyr Leu Ala Ala Ser Leu Val
1               5                   10                  15

Val Phe Thr Asn Tyr Ser Gly Asp Thr Ala Ser Gln Val Asp Val Asn
            20                  25                  30

Gly Pro Arg Ala Met Val Asp Asp Asp Lys Cys His Tyr Ala Asp
        35                  40                  45

Ala Ile Phe Thr Asn Ser Tyr Arg Lys Val Leu Gly Gln Leu Ser Ala
    50                  55                  60

Arg Lys Leu Leu Gln Asp Ile Met Ser Arg Gln Gln Gly Glu Ser Asn
65                  70                  75                  80

Gln Glu Arg Gly Ala Arg Ala Arg Leu Cys His
                85                  90

<210> SEQ ID NO 2
<211> LENGTH: 90
<212> TYPE: PRT
<213> ORGANISM: Artificial Sequence
<220> FEATURE:
<223> OTHER INFORMATION: Polypeptide

<400> SEQUENCE: 2

Arg Gly Ser Gly Gln Gly Gln Ala Gln Tyr Leu Ala Ala Ser Leu Val
1               5                   10                  15

Val Phe Thr Asn Tyr Ser Gly Asp Thr Ala Ser Gln Val Asp Val Asn
            20                  25                  30

Gly Pro Arg Ala Met Val Asp Asp Asp Lys Cys His Tyr Ala Asp
        35                  40                  45

Ala Ile Phe Thr Asn Ser Tyr Arg Lys Val Leu Gly Gln Leu Ser Ala
    50                  55                  60

Arg Lys Leu Leu Gln Asp Ile Met Ser Arg Gln Gln Gly Glu Ser Asn
65                  70                  75                  80

Gln Glu Arg Gly Ala Arg Ala Arg Leu Ala
                85                  90

<210> SEQ ID NO 3
<211> LENGTH: 80
<212> TYPE: PRT
<213> ORGANISM: Artificial Sequence
<220> FEATURE:
<223> OTHER INFORMATION: Polypeptide

<400> SEQUENCE: 3

Arg Gly Ser Gly Gln Gly Gln Ala Gln Tyr Leu Ala Ala Ser Leu Val
1               5                   10                  15

Val Phe Thr Asn Tyr Ser Gly Asp Thr Ala Ser Gln Val Asp Val Asn
            20                  25                  30

Pro Glu Phe Ser Val Gly Gly Gly Gly Pro Arg Cys His Ser Val
        35                  40                  45

Ser Glu Ile Gln Leu Met His Asn Leu Gly Lys His Leu Asn Ser Met

```
                    50                  55                  60
Glu Arg Val Glu Trp Leu Arg Lys Lys Leu Gln Asp Val His Asn Phe
 65                  70                  75                  80

<210> SEQ ID NO 4
<211> LENGTH: 130
<212> TYPE: PRT
<213> ORGANISM: Artificial Sequence
<220> FEATURE:
<223> OTHER INFORMATION: Polypeptide

<400> SEQUENCE: 4

Arg Gly Ser Gly Gln Gly Gln Ala Gln Tyr Leu Ala Ala Ser Leu Val
  1               5                  10                  15

Val Phe Thr Asn Tyr Ser Gly Asp Thr Ala Ser Gln Val Asp Val Asn
                 20                  25                  30

Pro Glu Phe Ser Val Gly Gly Gly Gly Pro Arg Cys His Ser Val
             35                  40                  45

Ser Glu Ile Gln Leu Met His Asn Leu Gly Lys His Leu Asn Ser Met
         50                  55                  60

Glu Arg Val Glu Trp Leu Arg Lys Lys Leu Gln Asp Val His Asn Phe
 65                  70                  75                  80

Val Ala Leu Gly Ala Pro Leu Ala Pro Arg Asp Ala Gly Ser Gln Arg
                 85                  90                  95

Pro Arg Lys Lys Glu Asp Asn Val Leu Val Glu Ser His Glu Lys Ser
            100                 105                 110

Leu Gly Glu Ala Asp Lys Ala Asp Val Asn Val Leu Thr Lys Ala Lys
        115                 120                 125

Ser Gln
    130

<210> SEQ ID NO 5
<211> LENGTH: 64
<212> TYPE: PRT
<213> ORGANISM: Artificial Sequence
<220> FEATURE:
<223> OTHER INFORMATION: Polypeptide

<400> SEQUENCE: 5

Arg Gly Ser Gly Gln Gly Gln Ala Gln Tyr Leu Asp Asp Asp Lys
  1               5                  10                  15

Cys His Tyr Ala Asp Ala Ile Phe Thr Asn Ser Tyr Arg Lys Val Leu
                 20                  25                  30

Gly Gln Leu Ser Ala Arg Lys Leu Leu Gln Asp Ile Met Ser Arg Gln
             35                  40                  45

Gln Gly Glu Ser Asn Gln Glu Arg Gly Ala Arg Ala Arg Leu Cys His
         50                  55                  60

<210> SEQ ID NO 6
<211> LENGTH: 7
<212> TYPE: PRT
<213> ORGANISM: Artificial Sequence
<220> FEATURE:
<223> OTHER INFORMATION: polypeptide

<400> SEQUENCE: 6

Ala Ala Cys His Gly Gly Gly
  1               5

<210> SEQ ID NO 7
<211> LENGTH: 4
```

```
<212> TYPE: PRT
<213> ORGANISM: Artificial Sequence
<220> FEATURE:
<223> OTHER INFORMATION: polypeptide

<400> SEQUENCE: 7

Ala Ala Cys His
1

<210> SEQ ID NO 8
<211> LENGTH: 44
<212> TYPE: PRT
<213> ORGANISM: Artificial Sequence
<220> FEATURE:
<223> OTHER INFORMATION: Polypeptide

<400> SEQUENCE: 8

Arg Gly Ser Gly Gln Gly Gln Ala Gln Tyr Leu Ala Ala Ser Leu Val
1               5                   10                  15

Val Phe Thr Asn Tyr Ser Gly Asp Thr Ala Ser Gln Val Asp Val Asn
            20                  25                  30

Pro Glu Phe Ser Val Gly Gly Gly Gly Gly Pro Arg
        35                  40

<210> SEQ ID NO 9
<211> LENGTH: 4
<212> TYPE: PRT
<213> ORGANISM: Artificial Sequence
<220> FEATURE:
<223> OTHER INFORMATION: Polypeptide

<400> SEQUENCE: 9

Asp Asp Asp Asp
1

<210> SEQ ID NO 10
<211> LENGTH: 4
<212> TYPE: PRT
<213> ORGANISM: Artificial Sequence
<220> FEATURE:
<223> OTHER INFORMATION: Polypeptide

<400> SEQUENCE: 10

Asp Asp Asp Lys
1

<210> SEQ ID NO 11
<211> LENGTH: 4
<212> TYPE: PRT
<213> ORGANISM: Artificial Sequence
<220> FEATURE:
<223> OTHER INFORMATION: Polypeptide

<400> SEQUENCE: 11

Asp Thr Arg Leu
1

<210> SEQ ID NO 12
<211> LENGTH: 4
<212> TYPE: PRT
<213> ORGANISM: Artificial Sequence
<220> FEATURE:
<223> OTHER INFORMATION: Polypeptide

<400> SEQUENCE: 12

Gly Gly Pro Arg
1
```

<210> SEQ ID NO 13
<211> LENGTH: 306
<212> TYPE: DNA
<213> ORGANISM: Artificial Sequence
<220> FEATURE:
<223> OTHER INFORMATION: Nucleotide sequence encoding chimeric
      polypeptide

<400> SEQUENCE: 13
atggctagca tgactggtgg acagcaaatg ggtcgcggat ccggccaggg acaggctcaa      60
tatctagcgg cctccttggt tgtgttcacc aactactcgg gcgacacggc cagccaggtg     120
gacgttaacg gtccgcgtgc tatggtcgac gacgacgaca atgccacta cgctgacgct     180 atcttcacca actcttaccg taaagttctg ggtcagctgt ctgctcgtaa actgctgcag     240
gacatcatgt cccgtcagca gggtgaatct aaccaggaac gtggtgctcg tgctcgtctg     300
gcataa                                                                306

<210> SEQ ID NO 14
<211> LENGTH: 101
<212> TYPE: PRT
<213> ORGANISM: Artificial Sequence
<220> FEATURE:
<223> OTHER INFORMATION: polypeptide

<400> SEQUENCE: 14

Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Val Asn Gly Pro Arg Ala Met
        35                  40                  45

Val Asp Asp Asp Asp Lys Cys His Tyr Ala Asp Ala Ile Phe Thr Asn
    50                  55                  60

Ser Tyr Arg Lys Val Leu Gly Gln Leu Ser Ala Arg Lys Leu Leu Gln
65                  70                  75                  80

Asp Ile Met Ser Arg Gln Gln Gly Glu Ser Asn Gln Glu Arg Gly Ala
                85                  90                  95

Arg Ala Arg Leu Ala
            100

<210> SEQ ID NO 15
<211> LENGTH: 309
<212> TYPE: DNA
<213> ORGANISM: Artificial Sequence
<220> FEATURE:
<223> OTHER INFORMATION: nucleotide sequence encoding chimeric
      polypeptide

<400> SEQUENCE: 15
atggctagca tgactggtgg acagcaaatg ggtcgcggat ccggccaggg acaggctcaa      60
tatctagcgg cctccttggt tgtgttcacc aactactcgg gcgacacggc cagccaggtg     120
gacgttaacg gtccgcgtgc tatggtcgac gacgacgaca atgccacta cgctgacgct     180 atcttcacca actcttaccg taaagttctg ggtcagctgt ctgctcgtaa actgctgcag     240
gacatcatgt cccgtcagca gggtgaatct aaccaggaac gtggtgctcg tgctcgtctg     300
tgccactaa                                                             309

<210> SEQ ID NO 16

<211> LENGTH: 102
<212> TYPE: PRT
<213> ORGANISM: Artificial Sequence
<220> FEATURE:
<223> OTHER INFORMATION: polypeptide

<400> SEQUENCE: 16

Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Val Asn Gly Pro Arg Ala Met
        35                  40                  45

Val Asp Asp Asp Lys Cys His Tyr Ala Asp Ala Ile Phe Thr Asn
    50                  55                  60

Ser Tyr Arg Lys Val Leu Gly Gln Leu Ser Ala Arg Lys Leu Leu Gln
65                  70                  75                  80

Asp Ile Met Ser Arg Gln Gln Gly Glu Ser Asn Gln Glu Arg Gly Ala
                85                  90                  95

Arg Ala Arg Leu Cys His
            100

<210> SEQ ID NO 17
<211> LENGTH: 276
<212> TYPE: DNA
<213> ORGANISM: Artificial Sequence
<220> FEATURE:
<223> OTHER INFORMATION: nucleotide sequence encoding chimeric
      polypeptide

<400> SEQUENCE: 17
atggctagca tgactggtgg acagcaaatg ggtcgcggat ccggccaggg tcaggctcaa      60
tatctggctg cctccctggt tgtgttcacc aactactcgg gcgacacggc cagccaggtg     120
gacgttaacc ggaattctc tgttggtggt ggtggtggtc cgcgttgcca ctctgtttct     180
gaaatccagc tgatgcacaa cctgggtaaa cacctgaact ctatggaacg tgttgaatgg     240
ctgcgtaaaa aactgcagga cgttcacaac ttctaa                               276

<210> SEQ ID NO 18
<211> LENGTH: 91
<212> TYPE: PRT
<213> ORGANISM: Artificial Sequence
<220> FEATURE:
<223> OTHER INFORMATION: polypeptide

<400> SEQUENCE: 18

Met Ala Ser Met Thr Gly Gly Gln Gln Met Gly Arg Gly Ser Gly Gln
1               5                   10                  15

Gly Gln Ala Gln Tyr Leu Ala Ala Ser Leu Val Val Phe Thr Asn Tyr
            20                  25                  30

Ser Gly Asp Thr Ala Ser Gln Val Asp Val Asn Pro Glu Phe Ser Val
        35                  40                  45

Gly Gly Gly Gly Pro Arg Cys His Ser Val Ser Glu Ile Gln Leu
    50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe
                85                  90

<210> SEQ ID NO 19

<211> LENGTH: 426
<212> TYPE: DNA
<213> ORGANISM: Artificial Sequence
<220> FEATURE:
<223> OTHER INFORMATION: nucleotide sequence encoding chimeric polypeptide

<400> SEQUENCE: 19

```
atggctagca tgactggtgg acagcaaatg ggtcgcggat ccggccaggg tcaggctcaa      60
tatctggctg cctccctggt tgtgttcacc aactactcgg gcgacacggc cagccaggtg     120
gacgttaacc cggaattctc tgttggtggt ggtggtggtc cgcgttgcca ctctgtttct     180
gaaatccagc tgatgcacaa cctgggtaaa cacctgaact ctatggaacg tgttgaatgg     240
ctgcgtaaaa aactgcagga cgttcacaac ttcgttgctc tgggtgctcc gctggctccg     300
cgtgacgctg ttcccagcg tccgcgtaaa aagaagaca cgttctggt tgaatcccac       360
gaaaaatccc tgggtgaagc tgacaaagct gacgttaacg ttctgaccaa agctaaatcc     420
cagtaa                                                                426
```

<210> SEQ ID NO 20
<211> LENGTH: 141
<212> TYPE: PRT
<213> ORGANISM: Artificial Sequence
<220> FEATURE:
<223> OTHER INFORMATION: polypeptide

<400> SEQUENCE: 20

```
Met Ala Ser Met Thr Gly Gly Gln Gln Met Gly Arg Gly Ser Gly Gln
1               5                   10                  15
Gly Gln Ala Gln Tyr Leu Ala Ala Ser Leu Val Val Phe Thr Asn Tyr
            20                  25                  30
Ser Gly Asp Thr Ala Ser Gln Val Asp Val Asn Pro Glu Phe Ser Val
        35                  40                  45
Gly Gly Gly Gly Gly Pro Arg Cys His Ser Val Ser Glu Ile Gln Leu
    50                  55                  60
Met His Asn Leu Gly Lys His Leu Asn Ser Met Glu Arg Val Glu Trp
65                  70                  75                  80
Leu Arg Lys Lys Leu Gln Asp Val His Asn Phe Val Ala Leu Gly Ala
                85                  90                  95
Pro Leu Ala Pro Arg Asp Ala Gly Ser Gln Arg Pro Arg Lys Lys Glu
            100                 105                 110
Asp Asn Val Leu Val Glu Ser His Glu Lys Ser Leu Gly Glu Ala Asp
        115                 120                 125
Lys Ala Asp Val Asn Val Leu Thr Lys Ala Lys Ser Gln
    130                 135                 140
```

<210> SEQ ID NO 21
<211> LENGTH: 48
<212> TYPE: PRT
<213> ORGANISM: Artificial Sequence
<220> FEATURE:
<223> OTHER INFORMATION: polypeptide

<400> SEQUENCE: 21

```
Cys His Tyr Ala Asp Ala Ile Phe Thr Asn Ser Tyr Arg Lys Val Leu
1               5                   10                  15
Gly Gln Leu Ser Ala Arg Lys Leu Leu Gln Asp Ile Met Ser Arg Gln
            20                  25                  30
Gln Gly Glu Ser Asn Gln Glu Arg Gly Ala Arg Ala Arg Leu Cys His
        35                  40                  45
```

```
<210> SEQ ID NO 22
<211> LENGTH: 46
<212> TYPE: PRT
<213> ORGANISM: Artificial Sequence
<220> FEATURE:
<223> OTHER INFORMATION: Polypeptide

<400> SEQUENCE: 22

Arg Gly Ser Gly Gln Gly Gln Ala Gln Tyr Leu Ala Ala Ser Leu Val
1               5                   10                  15

Val Phe Thr Asn Tyr Ser Gly Asp Thr Ala Ser Gln Val Asp Val Asn
                20                  25                  30

Pro Glu Phe Ser Val Gly Gly Gly Gly Pro Arg Cys His
            35                  40                  45
```